United States Patent
Shimizu et al.

(10) Patent No.: US 9,592,011 B2
(45) Date of Patent: Mar. 14, 2017

(54) POSITION-DETECTING DEVICE, RESPIRATION MEASUREMENT DEVICE AND HEART RATE MEASUREMENT DEVICE

(71) Applicant: SUMITOMO RIKO COMPANY LIMITED, Aichi (JP)

(72) Inventors: Atsuki Shimizu, Aichi (JP); Ichinosuke Maeda, Aichi (JP)

(73) Assignee: SUMITOMO RIKO COMPANY LIMITED, Aichi (JP)

( * ) Notice: Subject to any disclaimer, the term of this patent is extended or adjusted under 35 U.S.C. 154(b) by 0 days.

(21) Appl. No.: 14/799,980

(22) Filed: Jul. 15, 2015

(65) Prior Publication Data

US 2015/0351694 A1 Dec. 10, 2015

Related U.S. Application Data

(63) Continuation of application No. PCT/JP2014/053032, filed on Feb. 10, 2014.

(30) Foreign Application Priority Data

Feb. 12, 2013 (JP) ................................. 2013-024181

(51) Int. Cl.
*A61B 5/00* (2006.01)
*A61B 5/024* (2006.01)
(Continued)

(52) U.S. Cl.
CPC ........ *A61B 5/6892* (2013.01); *A61B 5/02444* (2013.01); *A61B 5/0816* (2013.01);
(Continued)

(58) Field of Classification Search
CPC ......... A61B 5/0053; A61B 5/024; A61B 5/08; A61B 5/6892; A61B 5/02444; A61B 5/0816; A61B 5/11; A61B 5/1116; A61B 5/4806

See application file for complete search history.

(56) References Cited

U.S. PATENT DOCUMENTS 6,306,088 B1 * 10/2001 Krausman .......... A61B 5/02055
600/301
2005/0107722 A1 5/2005 Ozaki et al.
(Continued)

FOREIGN PATENT DOCUMENTS

JP 07-163622 6/1995
JP 2000-316832 11/2000
(Continued)

OTHER PUBLICATIONS

International Search Report in PCT/JP2014/053032, dated Apr. 28, 2014.
(Continued)

*Primary Examiner* — Scott Getzow
(74) *Attorney, Agent, or Firm* — Greenblum & Bernstein, P.L.C.

(57) ABSTRACT

A position-detecting device includes a body pressure distribution sensor including a plurality of pressure sensors that outputs pressure signals corresponding to pressure values respectively and are arranged in a matrix pattern, a specific pattern storage unit storing a range that pressure sensors can occupy and a condition of pressure values relating to the pressure sensors within the range as a specific pattern by sleeping posture and body part of a sleeper, a scanning unit applying the specific pattern to body pressure distribution information, which is a set of the pressure values, from a scan starting position to an adjacent position in sequence and to determine whether the condition is satisfied, and a body (Continued)

part position determining unit determining the position of the body part in the sleeping posture corresponding to the position of the specific pattern in the body pressure distribution information when the condition is satisfied.

13 Claims, 13 Drawing Sheets

(51) Int. Cl.
  *A61B 5/08* (2006.01)
  *A61B 5/11* (2006.01)
  *A61B 5/113* (2006.01)
(52) U.S. Cl.
  CPC ............... *A61B 5/11* (2013.01); *A61B 5/1116* (2013.01); *A61B 5/4806* (2013.01); *A61B 5/113* (2013.01); *A61B 5/6891* (2013.01); *A61B 2562/0247* (2013.01); *A61B 2562/046* (2013.01)

(56) References Cited

U.S. PATENT DOCUMENTS

| | | | |
|---|---|---|---|
| 2005/0175225 A1 | 8/2005 | Shinzaki | |
| 2008/0312516 A1 | 12/2008 | Ozaki et al. | |
| 2014/0039351 A1* | 2/2014 | Mix | A61B 5/1114 600/587 |

FOREIGN PATENT DOCUMENTS

| | | |
|---|---|---|
| JP | 3321942 | 9/2002 |
| JP | 2005-144042 | 6/2005 |
| JP | 2005-160728 | 6/2005 |
| JP | 2005-204930 | 8/2005 |
| JP | 2005-222419 | 8/2005 |
| JP | 2006-263454 | 10/2006 |
| JP | 2007-517553 | 7/2007 |
| JP | 2009-199565 | 9/2009 |
| JP | 2009-240660 | 10/2009 |
| JP | 2010-063756 | 3/2010 |
| WO | 2012/021900 | 2/2012 |
| WO | 2012/122002 | 9/2012 |

OTHER PUBLICATIONS

Office Action issued in Japan Counterpart Patent Appl. No. 2013-024181, dated Aug. 23, 2016, along with an English translation thereof.

Machine translation of previously cited JP 2005-222419 published Aug. 18, 2005.

Machine translation of previously cited JP 2010-063756 published Mar. 25, 2010.

German Office Action, issued in the corresponding German Patent Application, dated Oct. 21, 2016, together with an English language translation thereof.

* cited by examiner

FIG.12A
FIG.12B
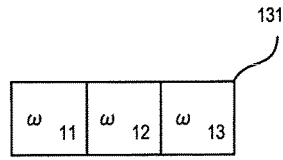
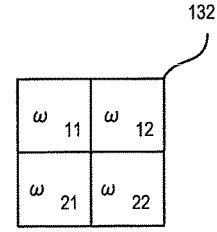

ns are changed, counts the number of the changes (see [0022] to [0033] and FIG. 1 and FIG. 3 of Japanese Patent No. 3321942).

POSITION-DETECTING DEVICE, RESPIRATION MEASUREMENT DEVICE AND HEART RATE MEASUREMENT DEVICE

This application is a Continuation of International Application No. PCT/JP2014/053032, filed on Feb. 10, 2014, which claims the benefit of Japanese Patent Application Number 2013-024181 filed on Feb. 12, 2013, the disclosures of which are incorporated by reference herein in their entireties.

BACKGROUND OF INVENTION

Technical Field

The present invention relates to a position-detecting device configured to detect positions of respective body parts of a sleeper using a body pressure distribution sensor including pressure sensors arranged in a matrix pattern. The present invention also relates to a respiration measurement device and a heart rate measurement device configured to detect a respiration measurement position and a heart rate measurement position of the sleeper using the position-detecting device to measure states of respiration and heart rate.

Background Art

There is known a sleeping apparatus configured to detect a body movement or a position of a sleeper and control reclining of a bed apparatus for a sit-up action of the sleeper on the basis of a detection result (see Japanese Patent No. 3321942 given below).

In the disclosed sleeping apparatus, pressure sensors arranged in a plane in the bed apparatus figure out a pressure distribution (constant pressure lines) of an entire body of the sleeper, then portions which receive large loads and correspond to centers of a body trunk of the sleeper are connected from a head portion to a leg portion, so that a shape of a sleeper's sleeping posture is determined.

Depending on the sleeping posture, a portion receiving a highest pressure at both ends of a line connecting the head portion and the leg portion respectively is determined to be a lower back, and the reclining of the bed apparatus is driven with the position of the lower back determined in this manner as a supporting point (see [0017], [0019], FIG. 2 to FIG. 4 of Japanese Patent No. 3321942).

Further, there is known a sleep monitoring apparatus configured to specify positions of respective body parts of a body in order to determine whether it is REM sleep or not on the basis of the number of body movement within a predetermined time (see Japanese Patent Application Publication No. 2000-316832 given below).

In the sleep monitoring apparatus, a sensor sheet having pressure-sensitive elements at a predetermined distribution is set on a bed. Characteristic amounts of the respective load distributions of the entire body in respective sleeping postures are recorded in a memory of a controller. The controller processes load signals from the respective pressure-sensitive elements of the sensor sheet, binarizes the load distributions of the whole, and obtains the characteristic amounts.

The controller collates the characteristic amounts of the respective load distributions in the memory and the characteristic amount of the load distribution of the sensor seat to detect a current sleeping posture of a user. The controller specifies positions of respective body parts (head portion, lower back portion, leg portion, both hands) on the basis of the detected sleeping posture, and when the specified posi-

SUMMARY OF INVENTION

With the conventional apparatuses, the pressure distribution of the entire body is obtained first, then, the entire distribution is analyzed to detect the positions of the respective body parts. Therefore, when detecting the position of the respective body parts, it is required to acquire the pressure distribution in a wide range and analyze the distribution, which results in increased information processing quantity.

Accordingly, the present invention is mainly intended to provide a position-detecting device configured to be capable of detecting positions of respective body parts of a sleeper efficiently, and a respiration measurement device and a heart rate measurement device utilizing the position-detecting device.

In order to achieve the above-described object, a first aspect of the invention is a position-detecting device including a body pressure distribution sensor, a specific pattern storage unit, a scanning unit and a body part position determining unit. The body pressure distribution sensor includes a plurality of pressure sensors that are capable of outputting pressure signals corresponding to pressure values respectively and are arranged in a matrix pattern having rows and columns. The body pressure distribution sensor is placed on bedclothes. The specific pattern storage unit is configured to store a range that can be occupied by the pressure sensors corresponding to a predetermined body part in a state in which a user takes a sleeping posture on the bedclothes and a condition of the pressure values of the pressure sensors within the range, as a specific pattern relating to the sleeping posture and the body part. The scanning unit is configured to apply the specific patterns to body pressure distribution information, which is a set of the plurality of pressure values in accordance with the matrix arrangement from a predetermined scan starting position to adjacent positions in a row direction or a column direction in sequence, and to determine whether the condition is satisfied in sequence. The body part position determining unit is configured to determine the position of the body part or a related body part in the corresponding sleeping posture relating thereto on the basis of the position of the specific pattern in the body pressure distribution information in the case where the scanning unit determines that the conditions are satisfied.

In the present invention, the pressure values may be any value as long as they correspond to the applied pressure, and may be converted into a value of a different form before processing, during processing, or after processing by the scanning unit or the like.

A second aspect of the invention is the above-described invention wherein the body part includes individual parts in pair of left part and right part or upper part and lower part of the user, and the related body part includes body parts relating to the pair of body parts. The scan starting position of the individual parts is the left part or the right part, or the upper part or the lower part in the body pressure distribution information depending on a position of the body parts in pair. The range of application of the specific patterns in sequence in the body pressure distribution information is limited to the left part or the right part, or the upper part or the lower part in the body pressure distribution information depending on the position of the individual body parts in pair.

A third aspect of the invention is the above-described invention wherein the condition is that the given pressure values corresponding to the number of the pressure sensors smaller than the number of the pressure sensors within a range which can be occupied by the pressure sensors are not smaller than a predetermined threshold value.

A fourth aspect of the invention is a respiration measurement device wherein at least one of the body part and the related body part is subjected to measurement of a chest respiration measurement value relating to chest respiration of the user on the basis of a chest position detected by the position-detecting device, which is a chest of the user.

A fifth aspect of the invention is the respiration measurement device characterized in that at least one of the body part and the related body part is subjected to measurement of an abdominal respiration measurement value relating to abdominal respiration by an abdominal part of the user on the basis of a lower-back position detected by the position-detecting device, which is a position of the lower back of the user.

A sixth aspect of the invention is the above-described invention further including a measurement value group autocorrelation securing unit that is configured to store a measurement value group in which the plurality of measurement values are accumulated for at least one of the chest respiration measurement value and the abdominal respiration measurement value. Further, the measurement value group autocorrelation securing unit is configured to exclude at least one of the chest respiration measurement value and the abdominal respiration measurement value, which has no autocorrelation with the measurement value group, from the measurement value group.

A seventh aspect of the invention is the above-described invention wherein pressure values are weighted depending on the arrangement of the pressure values at the detected chest position or lower-back position to measure the chest respiration measurement value or the abdominal respiration measurement value.

An eighth aspect of the invention is a heart rate measurement device wherein at least one of the body part and the related body part is subjected to measurement of a heart rate measurement value relating to heart rate of the user on the basis of the chest position detected by the position-detecting device, which is the chest of the user.

A ninth aspect of the invention is the above-described invention further including a heart rate measurement value group autocorrelation securing unit that is configured to store a heart rate measurement value group in which the plurality of heart rate measurement values are accumulated for the heart rate measurement value. Further, the heart rate measurement value group autocorrelation securing unit is configured to exclude the heart rate measurement value, which has no autocorrelation with the heart rate measurement value group, from the heart rate measurement value group.

A tenth aspect of the invention is the above-described invention wherein pressure values are weighted depending on the arrangement of the pressure values at the detected chest position to measure the heart rate measurement value.

According to the first aspect of the invention, position detection providing a high processing speed and an accurate processing result can be performed.

According to the second aspect of the invention, accurate detection with a scanning range meeting general arrangement relating to the user is achieved, and a processing quantity relating to scanning can be reduced adequately, so that position detection providing a higher processing speed and a more accurate processing result can be performed.

According to the third aspect of the invention, while characteristics of an outline of the body part is captured, individual differences, which are minute differences within the outline, can be absorbed, and further accurate position detection can be performed with little increase in the processing quantity.

According to the fourth and fifth aspects of invention, a respiration measurement device providing a high processing speed and an accurate processing result is provided.

According to the sixth aspect of the invention, the pressure values which have a tenuous connection with respiration can be discriminated, so that further accurate respiration measurement value group can be provided.

According to the seventh aspect of the invention, further accurate respiration measurement value based on an actual state of general users can be obtained.

According to the eighth aspect of the invention, a heart rate measurement device providing a high processing speed and an accurate processing result is provided.

According to the ninth aspect of the invention, the pressure values which have a tenuous connection with heart rate can be discriminated, so that further accurate heart rate measurement value group can be provided.

According to tenth aspect of the invention, further accurate heart rate measurement value based on an actual state of general users can be obtained.

BRIEF DESCRIPTION OF DRAWINGS

FIGS. 3A to 3D illustrate schematic drawings, in which FIG. 3A illustrates a supine shoulder specific pattern, FIG. 3B illustrates a supine lower-back specific pattern, FIG. 3C illustrates a lateral chest specific pattern, and FIG. 3D illustrates a lateral lower-back specific pattern in FIG. 1.

FIGS. 12A and 12B are schematic drawings of processing obtaining abdominal respiration measurement information from the respective pressure values during the processing in FIG. 11.

DETAILED DESCRIPTION OF EMBODIMENTS

Examples of the embodiments of the present invention and modifications will be described below with reference to the drawings as needed. The embodiments are not limited to the examples given below.

Figure 1:
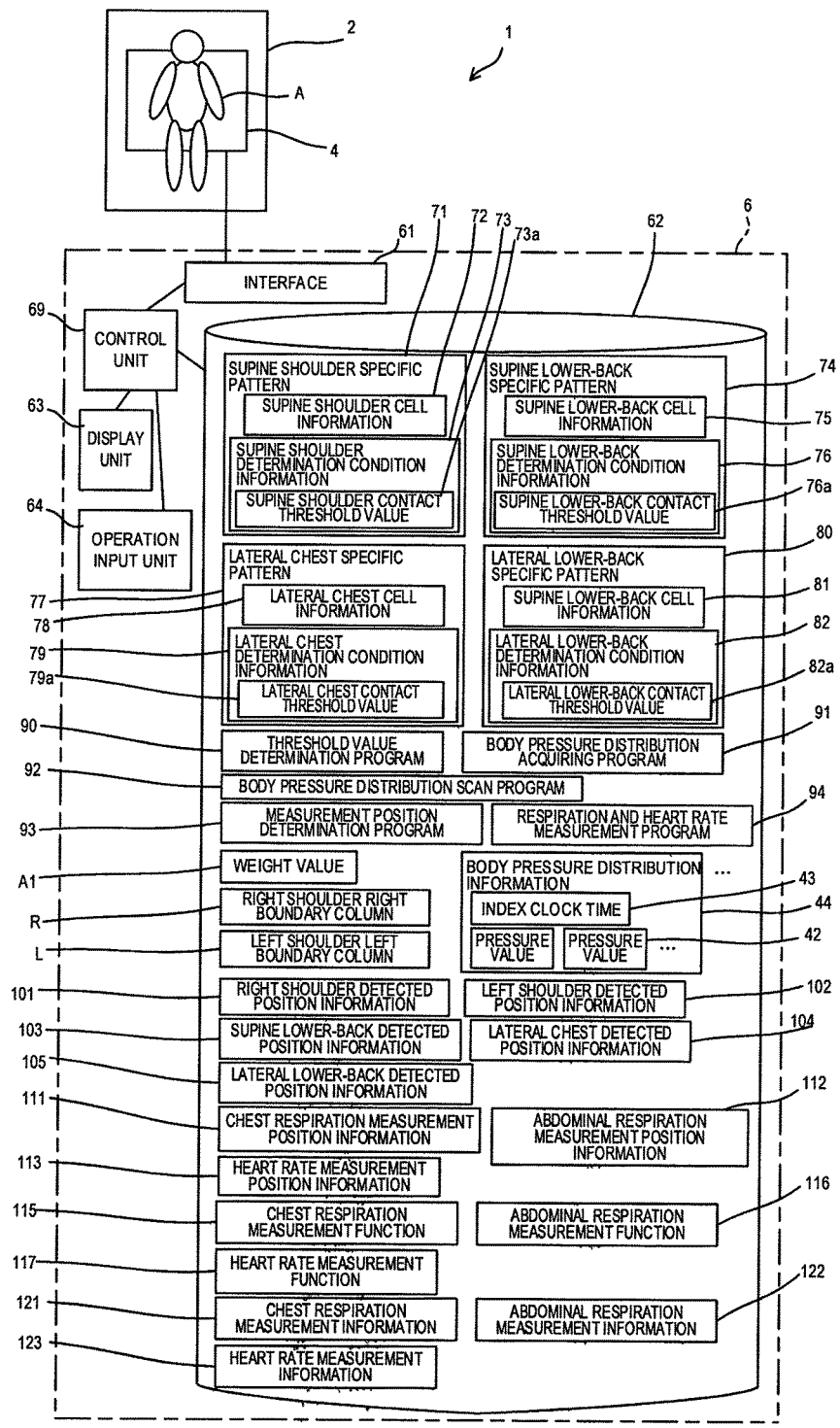
FIG. 1 is a schematic drawing illustrating a position-detecting device according to a first embodiment of the present invention.

FIG. 1 is a schematic drawing of a position-detecting device 1 according to a first embodiment of the present invention. The position-detecting device 1 includes bedclothes 2, a body pressure distribution sensor 4 placed on the bedclothes 2, and a computer 6.

The bedclothes 2 are equipment that allows a sleeper A as a user of the position-detecting device 1 to sleep thereon, and here, is a bed. However, mattress or Japanese-style bedding is also applicable.

Figure 2:
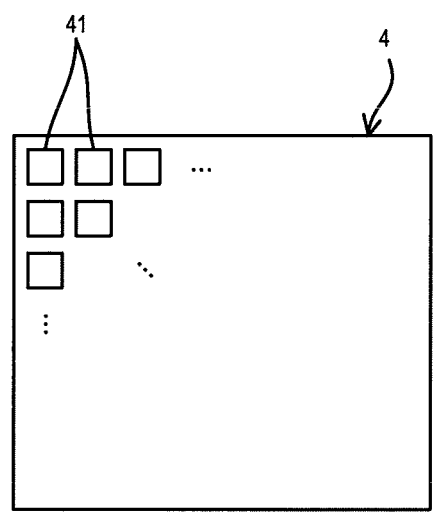
FIG. 2 is a schematic drawing of a body pressure distribution sensor in FIG. 1.

The body pressure distribution sensor 4 is a mat-like sensor having a plurality of pressure sensors 41, 41 . . . as illustrated in FIG. 2.

The pressure sensors 41, 41 . . . are arranged in a matrix pattern having rows and columns, and are arranged, for example, to have sixteen rows and sixteen columns. However, the numbers of the rows and the columns may be increased or decreased. The sizes of sensible ranges of the respective pressure sensors 41 may be set variously. In addition, even though the pressure sensors 41, 41 . . . are arranged in a zigzag pattern in a given column (or a given row), if the column (the row) can be set, it is considered to be arrangement of the matrix pattern.

The pressure sensors 41, 41 . . . are arranged over the entire body pressure distribution sensor 4. The pressure sensors 41, 41 . . . may be arranged only on part (center part or the like) of the body pressure distribution sensor 4.

The respective pressure sensors 41 are capable of outputting a pressure signal corresponding to a pressure value 42 relating to the pressure applied to the sensible area. The respective pressure sensors 41 may output the pressure signal in a form of the pressure value 42 as it in a predetermined unit, or may be output in another form corresponding to the pressure value 42 in the predetermined unit. That is, the pressure value 42 and the pressure signal may be set to any unit or form.

The body pressure distribution sensor 4 is placed on the surface of a portion of the bedclothes 2 where the sleeper A sleeps. The body pressure distribution sensor 4 has a length which covers from a neck portion to a femoral region of the sleeper A having a general adult body habitus, and has a width which is the same as the length. The body pressure distribution sensor 4 may be installed in the interior of the bedclothes 2. The length and the width of the body pressure distribution sensor 4 may by modified as needed such as a length which covers the entire sleeper A or a width smaller than the length.

The body pressure distribution sensor 4 is capable of outputting a set of the pressure values 42, 42 . . . detected by all of the pressure sensors 41 in the order corresponding to the positions of the pressure sensors 41, 41 . . . . Output of the set of the pressure values 42, 42 . . . is performed within a predetermined very short time (for example, approximately several tens of milliseconds). Further, the body pressure distribution sensor 4 is capable of outputting one set of the pressure values 42, 42 . . . and then outputting another set of the pressure values 42, 42 . . . at predetermined intervals (for example, approximately one second) and, in addition, is capable of outputting the set of the pressure values 42, 42 . . . repeatedly as needed. The very short time during which one set of the pressure values 42, 42 . . . are obtained may be changed, for example, from the interval of several milliseconds to the interval of one second, or from the interval of several seconds to the interval of dozen seconds, or to the interval of several tens of seconds. However, the shorter the time, the more processing performance is required, and the result becomes more accurate. The interval from the time when one set of the pressure values 42, 42 . . . are obtained to the time when the next pressure values 42, 42 . . . are obtained may be changed as needed.

Since the position-detecting device 1 discriminate the sets that the pressure values 42, 42 . . . belong to, a clock time within the very short time during which one set of the pressure values 42, 42 . . . are output (for example, the time of day when the very short time starts) is determined as an index clock time 43, and the respective sets of the pressure values 42, 42 . . . and the index clock time 43 are associated with each other. The sets of the pressure values 42, 42 . . . may be discriminated by assigning indexes different from each other such as assigning sequence number or assigning identification signs different from each other on the pressure values 42, 42 . . . at the time of output.

One set of the pressure values 42 at a certain index clock time 43 indicates a body pressure distribution relating to the index clock time 43, and information indicating the body pressure distribution associated with the index clock time 43 corresponds to body pressure distribution information 44. In other words, the body pressure distribution information 44 is a set of the pressure values 42, 42 . . . in which the pressure values 42, 42 . . . at the index clock time 43 are arranged in the order in accordance with the arrangement of the pressure sensors 41, 41 . . . in the body pressure distribution sensor 4.

The body pressure distribution sensor 4 may change into a configuration which outputs the pressure values 42, 42 . . . in a state of attaching information indicating the positions of the pressure sensors 41 showing the corresponding pressure values 42 to the respective pressure values. A configuration in which the body pressure distribution information 44 is obtained via computation on the body pressure distribution information 44 such as synchronizing the body pressure distribution information 44 relating to the plurality of index clock times 43 by averaging or the like. In this case, the index clock time 43 may be obtained by computation.

The computer 6 includes an interface 61 with respect to the body pressure distribution sensor 4, a storage unit 62 of information, a display unit 63, an operation input unit 64, and a control unit 69 for controlling the same.

Specific examples of the interface 61 include various terminals.

Specific examples of the storage unit 62 include a hard disk, a volatile or non-volatile memory, a memory disk and a drive therefor, and a combination of these members.

Specific examples of the display unit 63 include a flat display, a 7 segment display or a combination of these members.

Specific examples of the operation input unit 64 include a keyboard, a pointing device, and a combination thereof.

Specific examples of the control unit 69 include a CPU.

A supine shoulder specific pattern 71 used for detecting the position of the shoulder (blade bone) of the sleeper A in a supine position by scanning is stored in the storage unit 62.

Figure 3A:
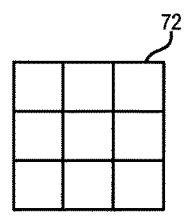

The supine shoulder specific pattern 71 includes supine shoulder cell information 72 and supine shoulder determination condition information 73 as illustrated in FIG. 3A.

The supine shoulder cell information 72 is information indicating a range for confirming cells C corresponding to the arbitrary pressure sensors 41 in sequence at the time of scanning the shoulder in the supine position, and includes cells C, C . . . arranged in three rows and three columns and adjacent to each other. In other words, the supine shoulder cell information 72 indicates that the range which can be occupied by the pressure sensors 41, 41 . . . corresponding to the shoulder in a state in which the general sleeper A takes a supine posture is determined to be the range of the cells C, C . . . arranged in three rows and three columns and adjacent to each other. The number of rows and columns in the supine shoulder cell information 72 may be increased and decreased.

The supine shoulder determination condition information 73 is information indicating conditions relating to the pressure values 42, 42 . . . at the cells C, C . . . in the supine shoulder cell information 72, and indicates a condition that the pressure values 42, 42 . . . at any three cells C, C . . . exceed a predetermined threshold value (supine shoulder contact threshold value 73a) out of nine cells C, C . . . indicated by the supine shoulder cell information 72 (then it is determined that the shoulder in the supine position is detected). In other words, the supine shoulder determination condition information 73 indicates that any three of the pressure values 42, 42 . . . are determined to exceed the supine shoulder contact threshold value 73a as the condition of the pressure values 42, 42 . . . within a range indicated by the supine shoulder cell information 72 which corresponds to the shoulder in the state in which the sleeper A takes the supine posture. The number of the cells C, C . . . which exceed the threshold value, presence or absence of limitation of positions of the cells C, C . . . exceeding the threshold value with respect to each other, and the number of types of the threshold values in the supine shoulder determination condition information 73 may be changed in a various manner.

The supine shoulder specific pattern 71 is used commonly when detecting the right shoulder and detecting the left shoulder as described later. The right shoulder and the left shoulder are various body parts of the sleeper A, paired on the left and right sides.

A supine lower-back specific pattern 74 used for detecting the position of the lower-back in a supine position of the sleeper A by scanning is stored in the storage unit 62.

Figure 3B:

The supine lower-back specific pattern 74 includes supine lower-back cell information 75 and supine lower back determination condition information 76 as illustrated in FIG. 3B.

The supine lower-back cell information 75 is information indicating a range of the cells C, C, . . . for confirming cells in sequence at the time of scanning the lower-back in the supine position, and includes cells C, C . . . adjacent to each other and arranged in one row and three columns. That is, the supine lower-back cell information 75 indicates that the range that can be occupied by the pressure sensors 41, 41 . . . corresponding to the lower back in a state in which the sleeper A takes a supine posture is determined to be arranged in one row and three columns and adjacent to each other.

The supine lower-back determination condition information 76 is information relating to a condition that all of the pressure values 42, 42 . . . of the three cells C, C . . . of the supine lower-back cell information 75 exceed a predetermined threshold value (supine lower-back contact threshold value 76a) (then it is treated as detection of the lower back in the supine position). That is, the supine lower-back determination condition information 76 indicates that any of the pressure values 42, 42 . . . are also determined to exceed the supine lower-back contact threshold value 76a as the condition of the pressure values 42, 42 . . . within a range indicated by the supine lower-back cell information 75 which corresponds to the lower back in the state in which the sleeper A takes the supine posture.

The supine lower-back specific pattern 74 may be changed in the same manner as the modification of the supine shoulder specific pattern 71.

In addition, a lateral chest specific pattern 77 used for detecting the chest position of the sleeper A in a lateral position by scanning is stored in the storage unit 62.

Figure 3C:
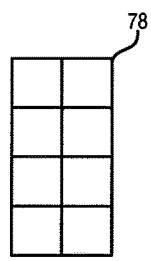

The lateral chest specific pattern 77 includes lateral chest cell information 78 and lateral chest determination condition information 79 as illustrated in FIG. 3C.

The lateral chest cell information 78 is information indicating a range of the cells C, C, . . . to be confirmed in sequence at the time of scanning the chest in the lateral position, and includes cells C, C . . . adjacent to each other and arranged in four rows and two columns. That is, the lateral chest cell information 78 indicates that the range that can be occupied by the pressure sensors 41, 41 . . . corresponding to the chest in a state in which the sleeper A takes a lateral posture is determined to be arranged in four rows and two columns and adjacent to each other.

The lateral chest determination condition information 79 is information relating to a condition that the pressure values 42, 42 . . . of the eight cells C, C . . . of the lateral chest cell information 78 exceed a predetermined threshold value (lateral chest contact threshold value 79a) (then it is treated as detection of the chest in the lateral position). That is, the lateral chest determination condition information 79 indicates that any of the pressure values 42, 42 . . . are also determined to exceed the lateral chest contact threshold value 79a as the condition of the pressure values 42, 42 . . . within a range indicated by the lateral chest cell information 78 which corresponds to the chest in the state in which the sleeper A takes the lateral posture.

The lateral chest specific pattern 77 may be changed in the same manner as the modification of the supine shoulder specific pattern 71.

In addition, a lateral lower-back specific pattern 80 used for detecting the lower-back position of the sleeper A in a lateral position by scanning is stored in the storage unit 62.

Figure 3D:
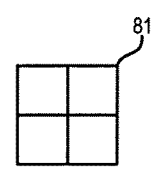

The lateral lower-back specific pattern 80 includes lateral lower-back cell information 81 and lateral lower-back determination condition information 82 as illustrated in FIG. 3D.

The lateral lower-back cell information 81 is information indicating a range of the cells C, C, . . . for confirming cells in sequence at the time of scanning the lower back in the lateral position, and includes cells C, C . . . adjacent to each other and arranged in two rows and two columns. That is, the lateral lower-back cell information 81 indicates that the range that can be occupied by the pressure sensors 41, 41 . . . corresponding to the lower back in a state in which the sleeper A takes a lateral posture is determined to be arranged in two rows and two columns and adjacent to each other.

The lateral lower-back determination condition information 82 is information relating to a condition that the pressure values 42, 42 . . . of the four cells C, C . . . of the lateral lower-back cell information 81 exceed a predetermined threshold value (lateral lower-back contact threshold value 82a) (then it is treated as detection of the lower back in the lateral position). That is, the lateral lower-back determination condition information 82 indicates that any of the pressure values 42, 42 . . . are also determined to exceed the lateral lower-back contact threshold value 82a as the condition of the pressure values 42, 42 . . . within a range indicated by the lateral lower-back cell information 81 which corresponds to the lower back in the state in which the sleeper A takes the lateral posture.

The lateral chest specific pattern 80 may be changed in the same manner as the modification of the supine shoulder specific pattern 71.

Difference between the supine position and the lateral position in the supine shoulder specific pattern 71, the supine lower-back specific pattern 74, the lateral chest specific pattern 77, and the lateral lower-back specific pattern 80 correspond to the difference in sleeping posture of the sleeper A, and the difference between the shoulder and the lower back corresponds to the difference in body part of the sleeper A.

The storage unit 62 configured to store the supine shoulder specific pattern 71, the supine lower-back specific pattern 74, the lateral chest specific pattern 77, and the lateral lower-back specific pattern 80 constitutes a specific pattern storage unit.

In addition, a threshold value determination program 90 for determining various threshold values, a body pressure distribution acquiring program 91 for acquiring the body pressure distribution relating to the respective index clock times 43 from the body pressure distribution sensor 4, a body pressure distribution scan program 92 configured to detect the respective parts (chest, lower back) of the body of the sleeper A by scanning the body pressure distribution, a measurement position determination program 93 for determining a range of the pressure sensors 41, 41 . . . configured to measure the respiration and the heart rate in accordance with the detected chest and lower-back position, and a respiration and heart rate measurement program 94 configured to obtain the measurement values of the respiration and the heart rate by computing the pressure values 42, 42 . . . in the range of the pressure sensors 41, 41 . . . are stored in the storage unit 62.

The control unit 69 detects a measurement positions for the respiration and the heart rate and performs measurement of the respiration and the heart rate by executing these programs as needed.

The control unit 69 is capable of combining respective programs or further segmentalizing the program.

A weight value A1, a right shoulder right boundary column R, and a left shoulder left boundary column L of the sleeper A described later are stored in the storage unit 62.

In addition, a right shoulder detected position information 101, a left shoulder detected position information 102, a supine lower-back detected position information 103, a lateral chest detected position information 104, a lateral lower-back detected position information 105, a chest respiration measurement position information 111, an abdominal respiration measurement position information 112, and a heart rate measurement position information 113 described later are stored in the storage unit 62.

In addition, a chest respiration measurement function 115, an abdominal respiration measurement function 116 (including weighting information 131, 132), a heart rate measurement function 117, a chest respiration measurement information 121, an abdominal respiration measurement information 122, and a heart rate measurement information 123 described later are stored in the storage unit 62.

Subsequently, an example of an action relating mainly to the position detection of the position-detecting device 1 will be described.

Figure 4:
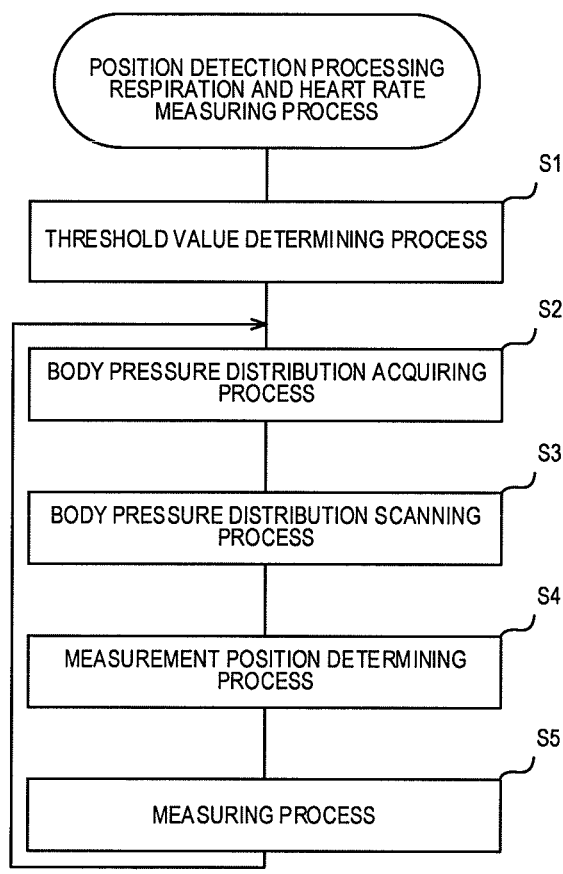
FIG. 4 is a flowchart of a process executed by the position-detecting device in FIG. 1.

FIG. 4 is a flowchart of a process executed by the position-detecting device 1.

The control unit 69 of the computer 6 executes the threshold value determination program 90, and performs a threshold value determination process S1 that determines various threshold values in accordance with the weight of the sleeper A.

In the threshold value determination process S1, the control unit 69 acquires the weight value A1 of the sleeper A by an input from an input unit 64, and values calculated from the input weight value A1 by using predetermined calculating formulas as the threshold values. For example, functions indicating changes of a pressure that the blade bones of various sleepers A applies on the bedclothes 2 in the supine position depending on the weight values are determined and stored in advance, and the control unit 69 substitutes the input weight value to the function into obtain the supine shoulder contact threshold value 73a. The supine lower-back contact threshold value 76a, the lateral chest contact threshold value 79a, and the lateral lower-back contact threshold value 82a are also the same.

The control unit 69 stores the obtained various threshold values into the storage unit 62.

The control unit 69 may estimate the weight value A1 from the initial body pressure distribution information 44, and calculate various threshold values from the estimated weight value A1. A configuration in which a weight measuring unit configured to measure the weight value A1 of the sleeper A is provided on the bedclothes 2. The control unit 69 obtains the weight value A1 from the weight measuring unit to obtain various threshold values from the weight value A1. In addition, it is also possible to omit the threshold value determination program 90 or the process based thereon and to use the predetermined threshold values.

Subsequently, the control unit 69 executes the body pressure distribution acquiring program 91 to perform a body pressure distribution acquiring process S2 in which the body pressure distribution information 44 in the same index clock time 43 is obtained from the body pressure distribution sensor 4 via the interface 61.

In the body pressure distribution acquiring process S2, the control unit 69 stores the body pressure distribution information 44 in the storage unit 62 in a state of including the index clock time 43.

The body pressure distribution sensor 4 may be configured to output the respective pressure values 42 in the body pressure distribution information 44 as a pressure value or a pressure signal of another form corresponding thereto. The control unit 69 may convert the pressure value or the pressure signal in the form of the pressure value 42.

Figure 5:
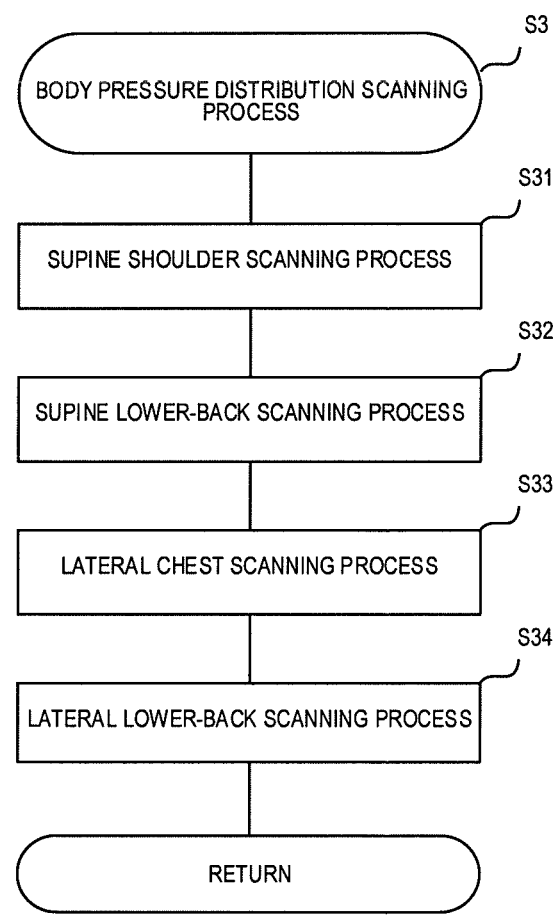
FIG. 5 is a flowchart illustrating details of a body pressure distribution scanning process in FIG. 4.

Subsequently, the control unit 69 executes the body pressure distribution scan program 92 to perform a body pressure distribution scanning process S3. FIG. 5 is a flowchart illustrating the body pressure distribution scanning process S3. The control unit 69 which executes the body pressure distribution scan program 92 and performs the body pressure distribution scanning process S3 constitutes a scanning unit.

The control unit 69 performs two scans with respect to the body pressure distribution information 44 in parallel as illustrated in FIG. 6 and FIG. 7 (supine shoulder scanning process S31, FIGS. 8A, 8B) relating to the shoulders in the supine position in the body pressure distribution scanning process S3. These two scans may be performed in sequence from the former (latter) first.

The scanning in FIG. 6 is intended to detect the right shoulder of the sleeper A in the supine position, and is performed from a first column to a predetermined column (the right shoulder right boundary column R, here, ninth column of sixteen columns) from a scan starting position at an upper left corner of the body pressure distribution information 44. Specifically, the scan starting position relating to the right shoulder is an upper left in the body pressure distribution information 44 in response to the fact that the right shoulder is arranged on the left in the supine position. A range in which fitting of the supine shoulder specific pattern 71 relating to the right shoulder is performed in sequence is limited to a left portion in the body pressure distribution information (by the right shoulder right boundary column R) in response to the position of the right shoulder.

The scanning process in FIG. 7 is intended to detect the left shoulder of the sleeper A in the supine position, and is performed from a specified column (the left shoulder left boundary column L, here, eighth column of sixteen columns) to the final column from a scan starting position at an upper right corner of the body pressure distribution information 44. Specifically, the scan starting position relating to the left shoulder is an upper right in the body pressure distribution information 44 in response to the fact that the left shoulder is arranged on the right in the supine position. A range in which fitting of the supine shoulder specific pattern 71 relating to the left shoulder is performed in sequence is limited to a right portion in the body pressure distribution information (by the left shoulder left boundary column L) in response to the position of the left shoulder.

By detecting the positions of the right shoulder portion and the left shoulder portion in pair, the position of the chest portion as a related body part having the right shoulder portion and the left shoulder portion can be detected as described later.

The first column of the body pressure distribution information 44 is a left end and the first row of the body pressure distribution information 44 is an upper end. The upper, lower, left and right of the body pressure distribution information 44 are positions when viewing the body pressure distribution sensor 4 from above, and the direction of the head of the sleeper A in the supine position is an upper direction, the direction of the leg is a lower direction, the direction of the right hand is a left direction, and the direction of the left hand is the right direction.

The right shoulder right boundary column R and the left shoulder left boundary column L may be changed variously. For example, these may be determined to be in the same column, or the right shoulder right boundary column R may be made smaller, but larger than the left shoulder left boundary column L so as to be positioned apart from each other. In contrast, the right shoulder right boundary column R may be made larger, but smaller than the left shoulder left boundary column L so as to widely overlap with each other.

In addition, part of the body pressure distribution information 44 may be excluded from the portion to be scanned in at least any scan processing, such as, omitting the rows of an upper and lower end or the columns on the left and right ends. In other words, the set of the pressure values 42, 42 . . . , as an object of the scan processing may be limited to part of a set of the pressure values 42, 42 . . . in a certain index time.

In the supine shoulder scanning process S31, the scan processing illustrated in FIG. 6 (supine right shoulder scanning process S31a in FIG. 8A) will be described.

Figure 8A:
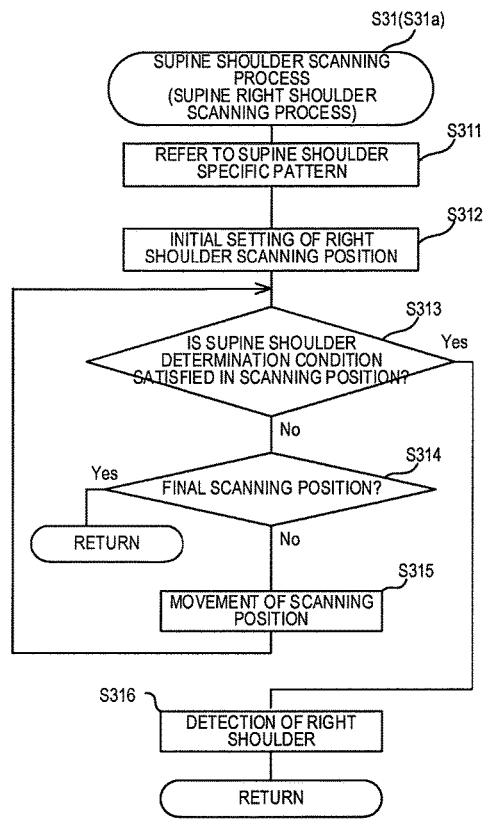
FIGS. 8A and 8B are flowcharts illustrating details of a supine shoulder scanning process in FIG. 5.

The control unit 69 figures out that the supine shoulder scanning process S31 for referring to the supine shoulder cell information 72 of the supine shoulder specific pattern 71 and detecting the shoulder in the supine position is performed with reference to the cells C, C . . . of three rows and three columns (Step S311 in FIG. 8A. In Step S311, it is figured out that the supine shoulder scanning process S31 for referring to the supine shoulder determination condition information 73 of the supine shoulder specific pattern 71 and detecting the shoulder in the supine position is performed on the basis whether any three of the pressure values 42, 42 . . . exceed the supine shoulder contact threshold value 73a out of the pressure values 42, 42 . . . in the set of the reference cells C, C . . . (the cells C, C . . . of three rows and three columns) as a criteria. Reference of the supine shoulder determination condition information 73 may be performed after the Step S312 described later.

Then, the control unit 69 performs an initial setting of the scanning position (Step S312). In other words, the control unit 69 determines a starting position of a scanning position B when scanning the right shoulder at the upper left corner of the body pressure distribution information 44 (first row, first column). The scanning position B of the right shoulder in the supine position is specified by focusing on the cell C at the upper left corner among the reference (three rows and three columns) cells C, C . . . . However, it may be specified by focusing on another cell C.

Subsequently, the control unit 69 determines whether or not the pressure values 42, 42 . . . of the cells C, C . . . at the scanning position B satisfies the conditions relating to the supine shoulder determination condition information 73 (Step S313).

Figure 6A:
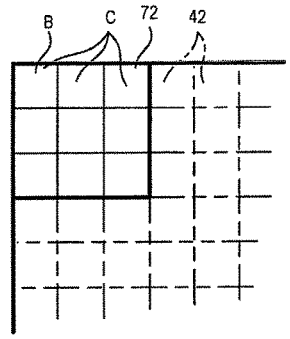
FIGS. 6A to 6D illustrates schematic drawings of processing for detecting a right shoulder in supine position during the body pressure distribution scanning process in FIG. 4.

Immediately after the start of scanning, the upper left corner of the body pressure distribution information 44 corresponds to the scanning position B as illustrated in FIG. 6A, and the pressure values 42, 42 . . . of the pressure sensors 41, 41 . . . in the reference cells C, C . . . at that position is referred to (from the first column to the third column of the first row, from the first column to the third column of the second row, and from the first column to the third column of the third row in the body pressure distribution information 44).

The control unit 69 refers to the pressure values 42, 42 . . . and the supine shoulder contact threshold value 73a to determine whether the condition is satisfied or not. If the condition is not satisfied (No in Step S313), the control unit 69 moves the scanning position B to the next position (Step S315) as long as it is not the last scanning position B (No in Step S314), and repeats Step 313. If it is the last scanning position B (Yes in Step S314), the procedures goes to next processing relating to the body pressure distribution information 44 of the index clock time 43.

In contrast, if the control unit 69 satisfies the condition (Yes in Step S313), the positions of the cells C, C . . . at the current scanning position B are determined to be the positions where the right shoulder exists, so that detection of the right shoulder is achieved (Step S316). The control unit 69 stores the information indicating the scanning position B (the positions of the cells C, C . . . ) in the storage unit 62 in a state in which the index clock time 43 of the scanned body pressure distribution information 44 is included as the right shoulder detected position information 101, and terminates the scanning process relating to the right shoulder without continuing any longer.

The movement of the scanning position B in Step S315 is performed in sequence in the following manner.

Figure 6B:
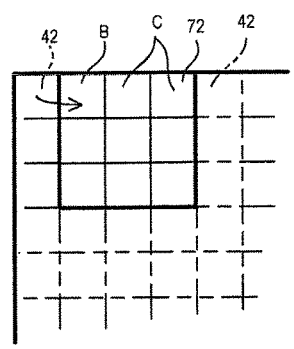
Figure 6C:
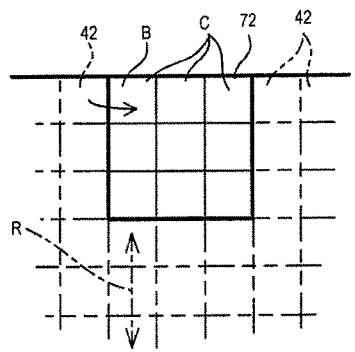

In other words, the control unit 69 moves the scanning position B from the starting position illustrated in FIG. 6A to the next column on the right side while staying in the same row as illustrated in FIG. 6B (from the second column to the fourth column of the first row, from the second column to the fourth column of the second row, from the second column to the fourth column of the third row in the body pressure distribution information 44).

Figure 6D:
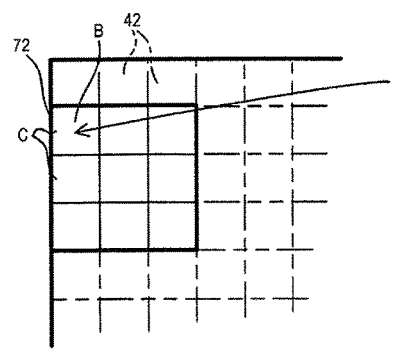

The control unit 69 moves the scanning position B rightward in sequence from one column to another in the same manner. When the scanning position B reaches a predetermined column (the right shoulder right boundary column R) (see FIG. 6C), the control unit 69 sets the left end of the next row as the next scanning position B as illustrated in FIG. 6D (from the first column to the third column of the second row, from the first column to the third column of the third row, and from the first column to the third column of the fourth row in the body pressure distribution information 44). The control unit 69 moves the scanning position B rightward in sequence from one column to another within the right shoulder right boundary column R in the next row as well.

The control unit 69 moves the scanning position B to the final scanning position B of the last row and the right shoulder right boundary column R unless the condition is satisfied (Yes) in Step 313 (see Step S314).

In the supine shoulder scanning process S31, the scan processing illustrated in FIG. 7 (supine left shoulder scanning process S31b in FIG. 8B) will be described.

Figure 8B:
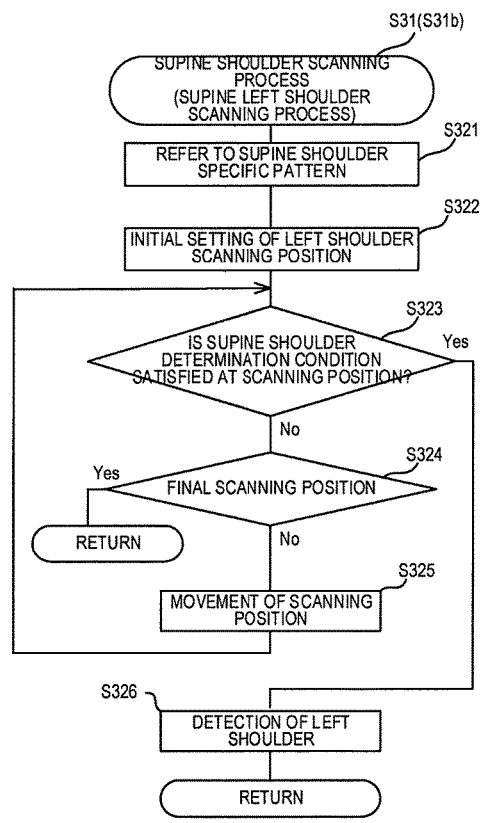

This scanning is performed in the substantially same manner as the scanning in FIG. 6 (Steps S311 to S316 in FIG. 8A) (Steps S321 to S326 in FIG. 8B).

The Step S321 is the same as the Step S311.

In the initial setting of the step S322, the scanning position B at the scan starting time is an upper right corner. The cell C to be focused at the time of the movement of the scanning position B at the reference cells C, C . . . is that at the upper right corner.

Step S323 is the same as Step S313, and Step S324 is the same as Step S314.

The movement of the scanning position B in Step S325 is performed in sequence in the following manner.

Figure 7A:
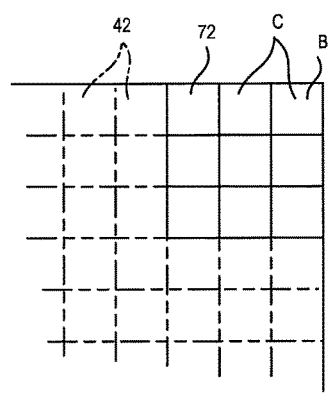
FIGS. 7A to 7D illustrate schematic drawings of processing for detecting a left shoulder in supine position during the body pressure distribution scanning process in FIG. 4.
Figure 7B:
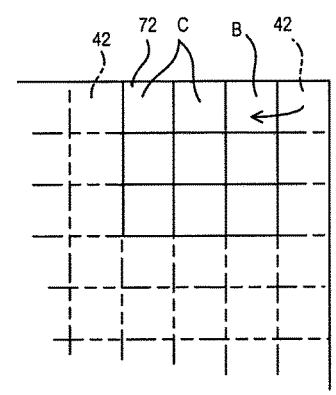
Figure 7C:
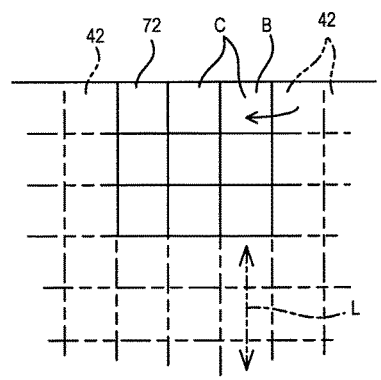

That is, the control unit 69 moves from the starting position illustrated in FIG. 7A (from the fourteenth column to the sixteenth column of the first row, from the fourteenth column to the sixteenth column of the second row, and from the fourteenth column to the sixteenth column of the third row in the body pressure distribution information 44) to the next column on the left side while staying in the same row as illustrated in FIG. 7B (from the thirteenth column to the fifteenth column of the first row, from the thirteenth column to the fifteenth column of the second row, from the thirteenth column to the fifteenth column of the third row in the body pressure distribution information 44).

Figure 7D:
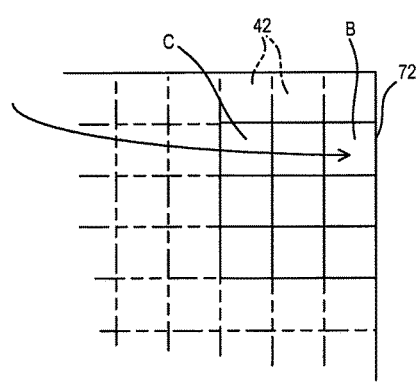

The control unit 69 moves the scanning position B leftward in sequence from one column to another in the same manner. When the scanning position B reaches a specific column (the left shoulder left boundary column L) (see FIG. 7C), the control unit 69 sets the right end of the next row as the next scanning position B as illustrated in FIG. 7D (from the fourteenth column to the sixteenth column of the second row, from the fourteenth column to the sixteenth column of the third row, and from the fourteenth column to the sixteenth column of the fourth row in the body pressure distribution information 44). The control unit 69 moves the scanning position B leftward in sequence from one column to another within the left shoulder left boundary column L in the next row as well.

The control unit 69 moves the scanning position B to the final scanning position B of the last row and the left shoulder left boundary column L unless the condition is satisfied (Yes) in Step 323 (see Step S324).

In contrast, the control unit 69 stores the information indicating the scanning position B (the positions of the cells C, C . . . ) in the storage unit 62 in a state of being associated with the index clock time 43 of the scanned body pressure distribution information 44 as the left shoulder detected position information 102. Then, the control unit 69 terminates the scanning process relating to the left shoulder without continuing any longer when the left shoulder is detected (Step S326).

It is possible to use the supine right shoulder cell information for the right shoulder and the supine left shoulder cell information for the left shoulder individually instead of the supine shoulder cell information 72. It is also possible to use the supine right shoulder determination condition information for the right shoulder (supine right shoulder contact threshold value) and supine left shoulder determination condition information for the left shoulder (supine left shoulder contact threshold value) instead of the supine shoulder determination condition information 73 (supine shoulder contact threshold value 73a).

In the supine lower-back scanning process S32, the control unit 69 detects the lower-back position at the supine position in the substantially same manner as the scanning of the right shoulder in the supine shoulder scanning process S31. In the supine lower-back scanning process S32, parallel dispersive detection such as simultaneous detection with separated scanning ranges for the right shoulder and the left shoulder is not performed. The supine lower-back scanning process S32 may be performed simultaneously with the supine shoulder scanning process S31, which applies to other scan processing as well.

Specifically, the control unit 69 moves the cells C, C . . . of one row and three columns indicated by the supine lower-back cell information 75 of the supine lower-back specific pattern 74 from the upper left corner of the body pressure distribution information 44 in sequence to the right and downward and whether the condition indicated by the supine lower-back determination condition information 76 is satisfied or not is determined every time. The control unit 69 determines the condition depending on whether all of the cells C, C . . . of one row and three columns exceed the supine lower-back contact threshold value 76a or not. In the scanning of the lower back in the supine position, there is no boundary such as the right shoulder right boundary column R, and a portion to the right end of the body pressure distribution information 44 is scanned, and then the scanning proceeds to the next row.

When the condition is determined to be satisfied, the control unit 69 stores the positions of the current reference cells C, C . . . (the scanning position B) in the storage unit 62 as the supine lower-back detected position information 103. Then, the control unit 69 terminates the scanning process relating to the lower back in the supine position.

The movement of the scanning position B (application of the various specific patterns in sequence) may be from the upper right to the lower left, or may be from the lower left to the upper right. Furthermore, the column at an end is scanned in a vertical direction, and then the scanning proceeds to the next column. In the scanning of the lower back in the supine position, any one of the cells C, C . . . among the reference cells C, C . . . may be focused. The modification exists in the same manner as needed in other scan processing.

In a lateral chest scanning process S33, the control unit 69 detects the chest position at the lateral position in the same manner as the scanning in the supine lower-back scanning process S32.

Specifically, the control unit 69 moves the cells C, C . . . of four rows and two columns indicated by the lateral chest cell information 78 of the lateral chest specific pattern 77 from an upper left corner of the body pressure distribution information 44 in sequence to the right and downward, and whether the condition indicated by the lateral chest determination condition information 79 is satisfied or not is determined every time. The control unit 69 determines the condition depending on whether all of the cells C, C . . . of four rows and two columns exceed the lateral chest contact threshold value 79a or not.

When the condition is determined to be satisfied, the control unit 69 stores the present scanning position B in the storage unit 62 as the lateral chest detected position information 104 in a state in which the index clock time 43 of the scanned body pressure distribution information 44 is included. Then, the control unit 69 completes the scanning process relating to the chest in the lateral position.

Furthermore, in a supine lower-back scanning process S34, the control unit 69 detects the lower-back position at the lateral position in the same manner as the scanning in the supine lower-back scanning process S32 and the lateral chest scanning process S33.

Specifically, the control unit 69 moves the cells C, C . . . of two rows and two columns indicated by the lateral lower-back cell information 81 of the lateral lower-back specific pattern 80 from the upper left corner of the body pressure distribution information 44 in sequence to the right and downward, and whether the condition indicated by the lateral lower-back determination condition information 82 is satisfied or not is determined every time. The control unit 69 determines the condition depending on whether all of the cells C, C . . . of two rows and two columns exceed the lateral lower-back contact threshold value 82a or not.

When the condition is determined to be satisfied, the control unit 69 stores the present scanning position B in the storage unit 62 as the lateral lower-back detected position information 105 in a state in which the index clock time 43 of the scanned body pressure distribution information 44 is included, and completes the scanning process relating to the lower-back in the lateral position.

The order of the scan relating to the shoulder or the lower back in a spine position, or the chest or the lower back in the lateral position may be modified in various manners in addition to the order described above. Further, part or the entire scanning process may be configured to be processed simultaneously. In the case where the lower back in the supine position is detected, the scanning of the lower back in the lateral position may be omitted, which applies to the both shoulders and the chest.

Figure 9:
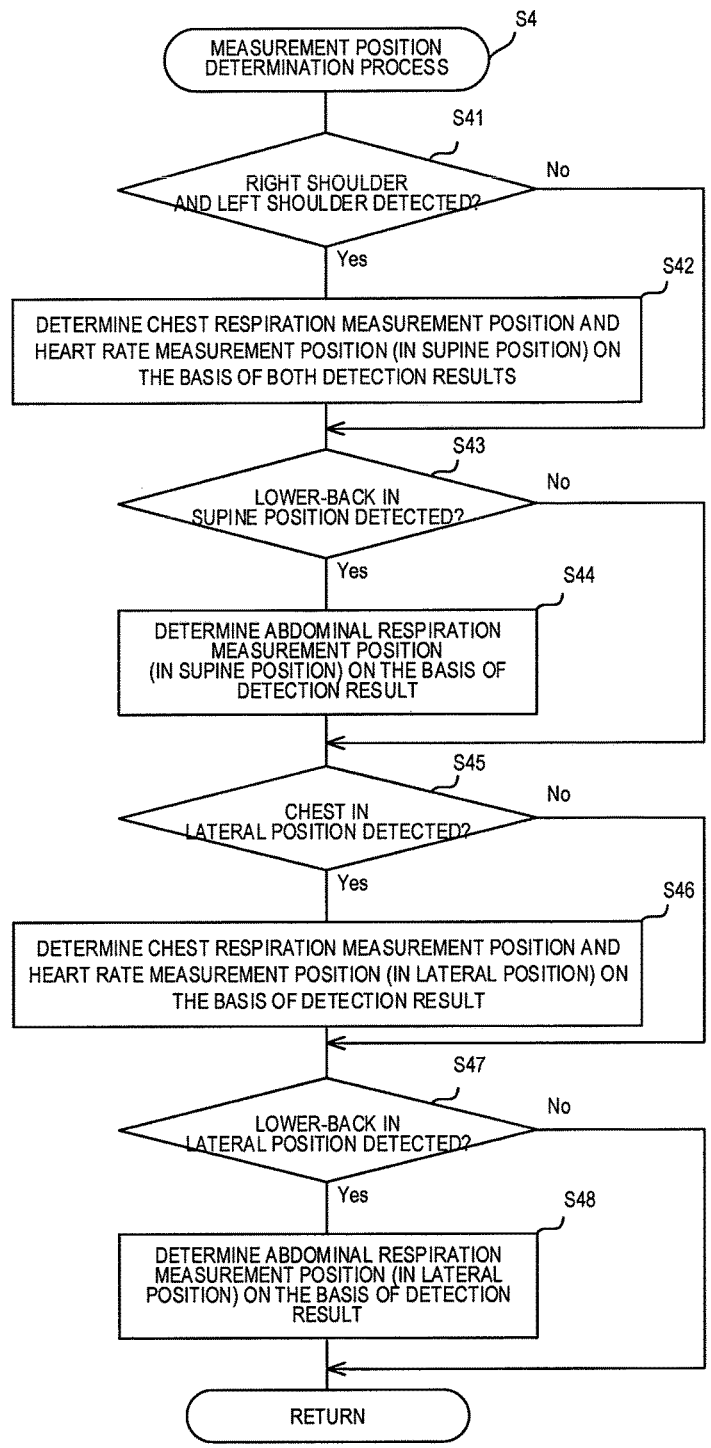
FIG. 9 is a flowchart illustrating details of a measurement position determination process in FIG. 4.

The control unit 69 executes a measurement position determination program 93, and performs a measurement position determination process S4 that determines the measurement position relating to the respiration and the heart rate as illustrated in FIG. 9. The control unit 69 executes the measurement position determination program 93, and the control unit 69 which performs the measurement position determination process S4 constitutes a body part position determining unit. The storage of the right shoulder detected position information 101, the left shoulder detected position information 102, the supine lower-back detected position information 103, the lateral chest detected position information 104, and the lateral lower-back detected position information 105 in the storage unit 62 by the control unit 69 may be considered to be the body part position determining unit.

If both of the right shoulder detected position information 101 and the left shoulder detected position information 102 relating to the same index clock time 43 exist (the right shoulder and the left shoulder are detected) in the measurement position determination process S4 (Yes in Step S41), the control unit 69 specifies the chest position (the area the chest occupies) of the sleeper A on the basis of the information, stores the chest position as the chest respiration measurement position information 111 in the storage unit 62, and stores in the storage unit 62 as the heart rate measurement position information 113 (Step S42).

Figure 10:
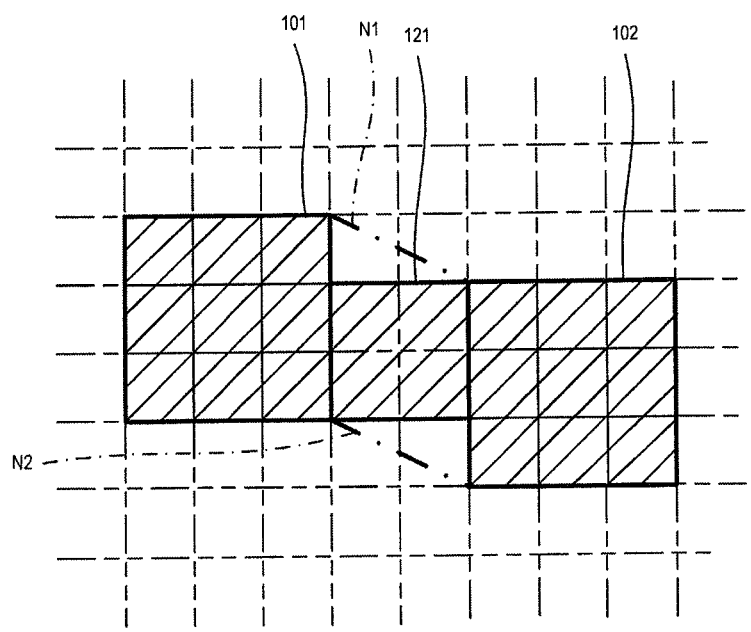
FIG. 10 is a schematic drawing illustrating processing for detecting a chest position from a right shoulder position and a left shoulder position during the processing in FIG. 9.

As illustrated in FIG. 10, the control unit 69 detects an area indicated by the right shoulder detected position information 101, an area indicated by the left shoulder detected position information 102, and an area therebetween (an expanded area 121 with respect to the right shoulder detected position information 101 and the left shoulder detected position information 102) as the chest position of the sleeper A (hatched portion).

The control unit 69 determines the expanded area 121 in the following manner. Specifically, the upper right corner of the area indicated by the right shoulder detected position information 101 and the upper left corner of the area indicated by the left shoulder detected position information 102 are connected by a line N1. The lower right corner of the area indicated by the right shoulder detected position information 101 and the lower left corner of the area indicated by the left shoulder detected position information 102 are connected by a line N2. A combination of a right side of the right shoulder detected position information 101, a left side of the left shoulder detected position information 102, and the pressure sensors 41, 41 . . . all of which are included within the range surrounded by the lines N1, N2 is determined as the expanded area 121.

An area combining the area indicated by the right shoulder detected position information 101 and the area indicated by the left shoulder detected position information 102 as is (an area in which the expanded area 121 is not included) may be detected as the chest position of the sleeper A. A specific area smaller than the area including the area indicated by the right shoulder detected position information 101 and the area indicated by the left shoulder detected position information 102 (and the expanded area) may be detected as the chest position. The expanded area may include the pressure sensors 41, 41 . . . where the lines N1, N2 pass, or may be determined as an area which is protruded in four directions by an amount equivalent to one pressure sensor 41 from the right shoulder detected position information 101 and the like without considering the lines N1, N2. In addition, the areas may be separated for the chest respiration measurement position information 111 and the heart rate measurement position information 113. Further, the body parts which corresponds to the head and the lower back, which is a pair of upper part and the lower part of the sleeper A, are detected by scanning that starts from the upper part or the lower part and limits to the upper part or the lower part, and the position of a back bone between these body parts may be determined as a position of the related body part.

The control unit 69 moves to the process of Step S43 after the Step S42 or in the case where one (or both) of the right shoulder detected position information 101 and the left shoulder detected position information 102 cannot be acquired (No in Step S41).

If the supine lower-back detected position information 103 exists (the lower back in the supine position is detected) at the index clock time 43 which is focused on (Yes in Step S43), the control unit 69 specifies the position of the lower back of the sleeper A on the basis of this information, and stores the position of the lower back in the storage unit 62 as the abdominal respiration measurement position information 112 in a state of including the index clock time 43 (Step S44).

The control unit 69 determines the range of the pressure sensors 41, 41 . . . indicated by the supine lower-back detected position information 103 to be the abdominal respiration measurement position information 112 as is.

It is also possible to set an expanded area with respect to the area indicated by the supine lower-back detected position information 103 for the abdominal respiration measurement position information 112 or to limit the abdominal respiration measurement position information 112 to a specific area in the area indicated by the supine lower-back detected position information 103, which applies in the following description.

The control unit 69 moves to processing of the Step S45 after Step S44 or when the lower back in the supine position is not detected (No in Step S43).

If the lateral chest detected position information 104 exists (the chest in the lateral position is detected) at the index clock time 43 which is focused on (Yes in Step S45), the control unit 69 specifies the position of the chest of the sleeper A on the basis of this information, and stores the position of the chest in the storage unit 62 as the chest respiration measurement position information 111 and the heart rate measurement position information 113 in a state of being associated with the index clock time 43 (Step S46).

The control unit 69 stores the range of the pressure sensors 41, 41 . . . indicated by the lateral chest detected position information 104 in the storage unit 62 as the chest respiration measurement position information 111 as is, and stores in the storage unit 62 as the heart rate measurement position information 113. As a matter of course, the area indicated by the chest respiration measurement position information 111 and the area indicated by the heart rate measurement position information 113 may be separated.

The control unit 69 moves to processing of the Step S47 after Step S46 or when the chest in the supine position is not detected (No in Step S45), the procedure goes to the process in Step S47.

If the lateral lower-back detected position information 105 exists (the lower back in the lateral position is detected) at the index clock time 43 which is focused on (Yes in Step S47), the control unit 69 specifies the position of the lower back of the sleeper A on the basis of this information, and stores in the storage unit 62 as the abdominal respiration measurement position information 112 in a state of including the index clock time 43 (Step S46).

The control unit 69 stores the range of the pressure sensors 41, 41 . . . indicated by the lateral lower-back detected position information 105 in the storage unit 62 as the abdominal respiration measurement position information 112 as is.

In the case where the lower back in the supine position is detected, a process of determining the abdominal respiration measurement position in the lateral position may be omitted, which applies to the both shoulders and the chest. It is also possible to synthesize the chest respiration measurement position information 111, the abdominal respiration measurement position information 112, and the heart rate measurement position information 113 (by employing the range of the pressure sensors 41, 41 . . . appearing more than a predetermined ratio out of the entire part) over a plurality of (predetermined) index clock times 43, and prepare the chest respiration measurement position information 111, the abdominal respiration measurement position information 112, and the heart rate measurement position information 113 which are synthesized with each other. The range of the plurality of index clock times 43 may be separated depending on the type of the information. In addition, the respective processes of determination of the chest and lower-back position in the supine or the lateral position in the measurement position determination process S4 may be performed in a latter half of the corresponding scan processing (any one of S31 to S34 in FIG. 5). It is also possible to separate (group) all (or most) of the pressure sensors 41, 41 . . . of the body pressure distribution sensor 4 on the basis of at least any one of the right shoulder detected position information 101, the left shoulder detected position information 102, the supine lower-back detected position information 103, the lateral chest detected position information 104, and the lateral lower-back detected position information 105, and determine one of the group as the chest respiration measurement position information 111 and the other one as the abdominal respiration measurement position information 112.

Subsequently, an example of an action relating mainly to the measurement of the position-detecting device 1 will be described.

The control unit 69 executes the respiration and heart rate measurement program 94 after the measurement position determination process S4, and performs a measurement process S5 (FIG. 4).

Figure 11:
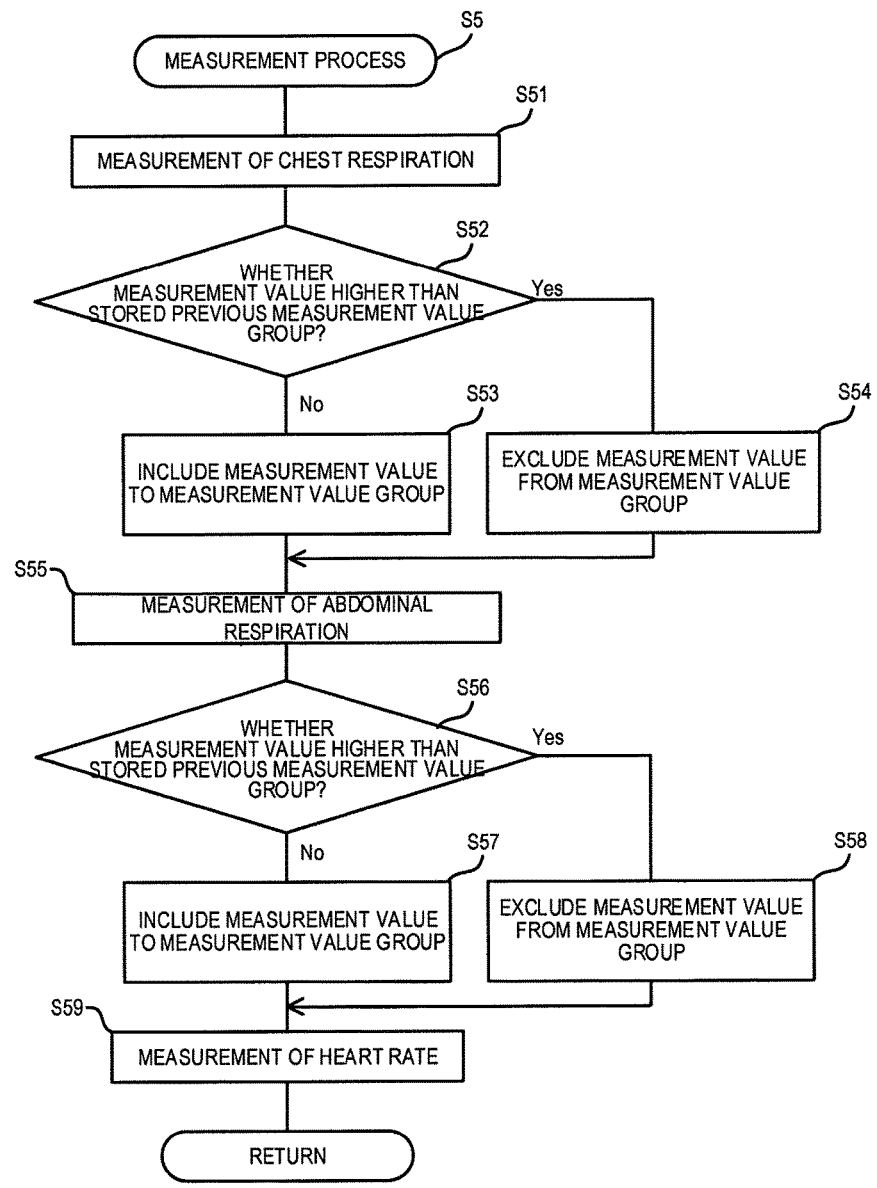
FIG. 11 is a flowchart illustrating details of a measurement process S5 in FIG. 4.

FIG. 11 is a flowchart of the measurement process S5 executed by the position-detecting device 1.

The control unit 69 computes the respective pressure values 42 of the pressure sensors 41, 41 . . . in a range indicated by the chest respiration measurement position information 111 using a predetermined function (the chest respiration measurement function 115), measures the chest respiration measurement information 121 indicating the state of the chest respiration (measurement value or the like such as the chest respiration pressure value), and stores the same in the storage unit 62 (Step S51). The chest respiration measurement information 121 corresponds to a chest respiration measurement value. A type configured to calculate an average value of all of the pressure values 42 within the corresponding range is employed here as the chest respiration measurement function 115. The chest respiration measurement function 115 may be changed to an average value of a high order predetermined number of the pressure value 42 within the corresponding range, which applies to other functions.

In addition, the control unit 69 accumulates the chest respiration measurement information 121 (the measurement value obtained by the chest respiration measurement function 115) from one index clock time 43 to another in the storage unit 62 as a measurement value group. Then, when more than the predetermined number of measurement values are accumulated as the measurement value group, the control unit 69 calculates an average value of the measurement values in the measurement value group, and determines whether or not the chest respiration measurement information 121 of this time (measurement value) is apart from the average value by a specific value or more (whether it is larger, in this case) (Step S52). If the measurement value is not higher than the average value of the measurement value group by a specific value or more (No in Step S52), the control unit 69 integrates the chest respiration measurement information 121 of this time into the measurement value group. If it is higher by more than the specific value (Yes in Step S52), the chest respiration measurement information 121 is not integrated into the measurement value group (Step S54). That is, the control unit 69 is capable of creating the measurement value group having autocorrelation with the measurement value group in the past by excluding the measurement values having no autocorrelation therewith (the measurement value group autocorrelation securing unit).

Subsequently, the control unit 69 computes the respective pressure values 42 of the pressure sensors 41, 41 . . . in a range indicated by the abdominal respiration measurement position information 112 using a predetermined function (the abdominal respiration measurement function 116), measures the abdominal respiration measurement information 122 indicating the state of the abdominal respiration (abdominal respiration pressure or the like), and stores the same in the storage unit 62 (Step 55). The abdominal respiration measurement information 122 corresponds to an abdominal respiration measurement value.

Now, the abdominal respiration measurement information 122 is obtained as the abdominal respiration measurement function 116 by weighting the respective pressure values 42 of the pressure sensors 41, 41 . . . within a range indicated by the abdominal respiration measurement position information 112 in accordance with the positions in the range as schematically illustrated in FIG. 12.

Specifically, in the case where the information in the supine position is obtained as the abdominal respiration measurement position information 112, like the weighting information 131 illustrated in FIG. 12A, in the abdominal respiration measurement position information 112 a pressure value 42 ($p_{11}$) in the first row and first column is multiplied by a weighting coefficient $\omega_{11}$, and a pressure value 42 ($p_{12}$) in the first row and second column is multiplied by a weighting coefficient $\omega_{12}$ and a pressure value 42 ($p_{13}$) in the first row and third column is multiplied by a weighting coefficient $\omega_{13}$, thereby obtaining the abdominal respiration measurement information 122. Here, the weighting coefficients $\omega_{11}$, $\omega_{13}$ are set to be larger than the weighting coefficient $\omega_{12}$, and thus weighting matches the general pressure distribution of the lower back in the supine position.

Further, in the case where the information in the lateral position is obtained as the abdominal respiration measurement position information 112, like the weighting information 132 illustrated in FIG. 12B, in the abdominal respiration measurement position information 112 the pressure value 42 ($p_{11}$) in the first row and first column is multiplied by the weighting coefficient $\omega_{11}$, and the pressure value 42 ($p_{12}$) in the first row and second column is multiplied by a weighting coefficient $\omega_{12}$, a pressure value 42 ($p_{21}$) in the second row and first column is multiplied by a weighting coefficient $\omega_{21}$, and a pressure value 42 ($p_{22}$) in the second row and second column is multiplied by a weighting coefficient $\omega_{22}$, thereby obtaining the abdominal respiration measurement information 122. The weighting coefficient $\omega_{11}$ or the weighting coefficient $\omega_{12}$ in the weighting information 132 may be differentiated from the weighting coefficient $\omega_{11}$ or the weighting coefficient $\omega_{12}$ in the weighting information 131. Here, the weighting coefficients $\omega_{11}$, $\omega_{12}$ are set to be larger than the weighting coefficient $\omega_{21}$, $\omega_{22}$, and thus weighting matches the general pressure distribution of the lower back in the lateral position. Such a weighting may be performed for the shoulder and the chest, or may be omitted as needed.

The acquisition of the weighted abdominal respiration measurement information 122 (abdominal respiration measurement value P) is expressed by Expression 1 as given below. Here, i denotes a row number (ith row) and k denotes a column number (kth column)

$$P = \sum_k \sum_i \omega_{ik} p_{ik} \qquad \text{[Expression 1]}$$

In the same manner as the chest respiration measurement information 121 described above (Steps S52 to S54), the measurement value group having autocorrelation are accumulated in the storage unit 62 in the abdominal respiration measurement information 122 as well (Steps S56 to S58, the measurement value group autocorrelation securing unit).

In addition, the control unit 69 computes the respective pressure values 42 of the pressure sensors 41, 41 . . . in a range indicated by the heart rate measurement position information 113 using a predetermined function (the heart rate measurement function 117), measures the heart rate measurement information 123 indicating the state of the heart rate (heart rate or the like), and stores the same in the storage unit 62 (Step 59). The heart rate measurement information 123 corresponds to the heart rate measurement value.

The measurement value group having autocorrelation is not created in the heart rate measurement information 123. However, the measurement value group may be created also in the heart rate measurement information 123. If the measurement value group is created in the heart rate measurement information 123, the heart rate measurement value group autocorrelation securing unit may be constituted. It is also possible not to create the measurement value group in the chest respiration measurement information 121 and the abdominal respiration measurement information 122.

With the acquisition of the chest respiration measurement information 121, the abdominal respiration measurement information 122, and the heart rate measurement information 123, the position-detecting device 1 also has a function as the respiration measurement device and the heart rate measurement device.

The control unit 69 displays the chest respiration measurement information 121, the abdominal respiration measurement information 122 and the heart rate measurement information 123, which are measured, on the display unit 63 on the basis of the operation input information from the operation input unit 64 as needed.

It is also possible to provide the position-detecting device 1 having only the position detection function by omitting the respiration and heart rate measurement program 94 and the respective measurement information. In this case, the control unit 69 may output various position information to an external (separate) measurement device. Part such as the respiration and heart rate measurement program 94 (portion of the abdominal respiration or portion of the heart rate, or both) may be omitted.

After the measurement process S5, the control unit 69 repeats the processes from the body pressure distribution acquiring process S2 relating to the next index clock time 43 as needed. If the presence of the state which should be terminated such as a case where a state in which all of the pressure values 42, 42 . . . in the body pressure distribution information 44 are a predetermined value (for example, 0) or smaller continues for a certain period is determined, the control unit 69 performs a final process which performs the computation or the storage of the respective information as needed and terminates the process.

The control unit 69 may be repeated from the threshold value determination process S1. Alternatively, the control unit 69 may process from the body pressure distribution acquiring process S2 to the measurement position determination process S4 and the measurement process S5 in parallel. In the latter processing, the control unit 69 may obtain the right shoulder detected position information 101, the left shoulder detected position information 102, the supine lower-back detected position information 103, the lateral chest detected position information 104, and the lateral lower-back detected position information 105 from the former processing as arbitrary timing. Alternatively, the various processing may be performed in parallel.

The position-detecting device 1 of the first embodiment includes the body pressure distribution sensor 4, the specific pattern storage unit, the scanning unit, and the body part position determining unit. The body pressure distribution sensor 4 includes the plurality of pressure sensors 41, 41 . . . which can output the pressure signals corresponding to the pressure values 42, 42 . . . from one index clock time 43 to another and are arranged in a matrix pattern having rows and columns. The body pressure distribution sensor 4 is placed on the bedclothes 2. The specific pattern storage unit (part of the storage unit 62) stores the range which can be occupied by the pressure sensors 41, 41 . . . corresponding to predetermined body parts (shoulder, chest or lower back) in a state in which the sleeper A takes a sleeping position (supine/lateral) on the bedclothes 2 (the supine shoulder cell information 72, the supine lower-back cell information 75, the lateral chest cell information 78, the lateral lower-back cell information 81) and conditions of the pressure values 42, 42 . . . of the pressure sensors 41, 41 . . . within the range thereof (the supine shoulder determination condition information 73, the supine lower-back determination condition information 76, the lateral chest determination condition information 79, the lateral lower-back determination condition information 82) as the specific pattern relating to the sleeping position and the body part (the supine shoulder specific pattern 71, the supine lower-back specific pattern 74, the lateral chest specific pattern 77, the lateral lower-back specific pattern 80). The scanning unit (the control unit 69 configured to perform the body pressure distribution scanning process S3) determines the conditions in sequence by applying the specific pattern to the body pressure distribution information 44, which is a set in accordance with the arrangement in the matrix pattern, of a plurality of the pressure values 42, 42 . . . relating to the arbitrary index clock time 43 from the predetermined scan starting position (upper left or upper right, upper left, upper left, upper left) to the adjacent position in the direction of the row or in the direction of the column in sequence (here, in the scanning form which moves to all of the columns in one row and then proceeds to the next row). The body part position determining unit (the control unit 69 configured to obtain the chest respiration measurement position information 111, the abdominal respiration measurement position information 112, the heart rate measurement position information 113) determines the position of the body part in the corresponding sleeping position (the both shoulder in the supine position, the lower back in the supine position, the chest in the lateral position, the lower back in the lateral position) or the related body part relating thereto (the chest in the supine position) on the basis of the position of the specific pattern in the body pressure distribution information 44 (the right shoulder detected position information 101, the left shoulder detected position information 102, the supine lower-back detected position information 103, the lateral chest detected position information 104, the lateral lower-back detected position information 105) in the case where the conditions are determined to be satisfied by the scanning unit.

Therefore, in the case where the pressure values 42, 42 . . . which match the specific pattern exist in the body pressure distribution information 44, it is not necessary to refer to the body pressure distribution information 44 from the matched pressure values 42, 42 . . . onward, so that the pressure values 42, 42 . . . which match the specific pattern, that is, the target body part can be detected accurately without determining all of the pressure values 42, 42 . . . of the body pressure distribution information 44. Therefore, position detection providing a high processing speed and an accurate processing result can be performed.

The sleeper A has the right shoulder and the left shoulder which are paired on the left and right sides as the body parts, and the chest relating to the pair of the right shoulder and the left shoulder as the related body part. The scan starting position relating to the right shoulder or the left shoulder is the left or the right in the body pressure distribution information 44 depending on the position of the right shoulder or the left shoulder. The range of application of the specific pattern in the body pressure distribution information 44 in sequence is limited to the left portion (the portion on the left side of the right shoulder right boundary column R) or the right portion (the portion on the right side of the left shoulder left boundary column L) in the body pressure distribution information 44 depending on the position of the pair of the right shoulder and the left shoulder.

Therefore, even when the sleeper A rotates to some extent with respect to the body pressure distribution sensor 4 (approximately less than 90°), or even though there is a difference in shoulder width (the distance between the right shoulder and the left shoulder) by the individual difference among a plurality of the sleepers A, A . . . , the right shoulder and the left shoulder in the supine position can be detected accurately, and the chest position in the supine position can be detected accurately. In addition, when detecting the right shoulder in the supine position, scanning may be performed only on the left portion of the body pressure distribution information 44, and when detecting the left shoulder in the supine position, scanning may be performed only on the right portion of the body pressure distribution information 44. Therefore, accurate detection is performed by the scanning range suitable to the general position of the right shoulder and the left shoulder in the supine position, and the processing amount relating to the scanning can be adequately reduced. Accordingly, positional detection with a high processing speed and an accurate processing result is realized.

In addition, the condition indicated by the supine shoulder determination condition information 73 is that all of the (three) arbitrary pressure values 42, 42 . . . , which is less than the number of the pressure sensors 41, 41 . . . (nine) in the range (the supine shoulder cell information 72) which can be occupied by the pressure sensors 41, 41 . . . become supine shoulder contact threshold value 73a or higher. Therefore, arbitrary three of the pressure values 42, 42 . . . out of the nine of the pressure sensors 41, 41 . . . can be set as the object to be determined of the supine shoulder contact threshold value 73a, so that the portion to be determined may be varied in the supine shoulder cell information 72 (the portion to be determined is variable). Therefore, while characteristics of an outline of the shoulder is captured (supine shoulder cell information 72), individual differences, which are minute differences within the outline, can be absorbed (variable), and further accurate position detection can be performed with little increase in the processing quantity.

In addition, the measurement value group autocorrelation securing unit is provided so as to store the chest respiration measurement value (the chest respiration measurement information 121) and the abdominal respiration measurement value (the abdominal respiration measurement information 122) as the measurement value group in which a plurality of measurement values are accumulated over the different index clock times 43. Further, the measurement value group autocorrelation securing unit excludes the chest respiration measurement value and the abdominal respiration measurement value, which have no autocorrelation with the measurement value group, from the measurement value group. Therefore, the pressure value 42 or the like caused by the body movement having no autocorrelation (larger than the average value by a specific value) in comparison with (the average value of) the pressure value 42 applied by the respiration, can be excluded, so that the measurement value group having higher reliability can be provided.

In addition, the control unit 69 weights the pressure values 42, 42 . . . depending on the arrangement of the pressure values 42, 42 . . . at the detected lower-back position (abdominal respiration measurement position information 112) (weighting information 131, 132) and measures the abdominal respiration measurement value (the abdominal respiration measurement information 122) (a weighting measuring unit). Therefore, further accurate abdominal respiration measurement information 122 based on an actual state of general sleeper A can be obtained.

In the case where the autocorrelation of the measurement value group is secured or weighting of the measurement value group is performed in the heart rate measurement, the same effects as those relating to the respiration described above are obtained also in the heart rate measurement.

A position-detecting device according to a second embodiment of the present invention is the same as the position-detecting device 1 according to the first embodiment except for the following points. In the second embodiment, the supine shoulder specific pattern 71 of the first embodiment is replaced by a supine chest specified pattern 271 illustrated in FIG. 13A and, accordingly, the supine shoulder scanning process S31 of the first embodiment changes correspondingly.

Figure 13A:
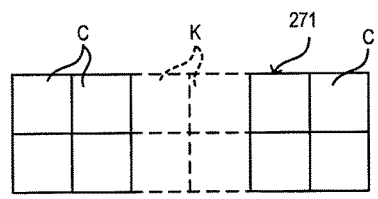
FIG. 13A is a schematic drawing of a supine chest specified pattern according to a second embodiment of the present invention.

In the second embodiment, as illustrated in FIG. 13A, the cells C, C . . . of two rows and two columns on the left side, the cells C, C . . . of two rows and two columns on the right side, and blank cells K, K . . . , which are blank, of two rows and two columns therebetween are used as the supine chest specified pattern 271.

The control unit 69 executes the supine chest scanning process instead of the supine shoulder scanning process S31 in the first embodiment. In this processing, the control unit 69 applies the supine chest specified pattern 271 to the body pressure distribution information 44 in sequence from the upper left corner, and performs scanning on the chest portion in the supine position. The reference cell C of the supine chest specified pattern 271 is the upper left corner. The condition of determining the chest portion here is that the sum (or an average) of the pressure values 42, 42 . . . at the eight cells C, C . . . in total is not smaller than the predetermined threshold value (supine chest contact threshold value). The pressure values 42, 42 . . . at the blank cells K, K, . . . are not used in the determination of the condition, and has a function to separate the cells C, C . . . on the left side and the cells C, C . . . on the right side used for the determination from each other. In addition, in the scanning of the chest in the supine position according to the second embodiment, the right shoulder right boundary column R and the left shoulder left boundary column L do not exist.

The number or arrangement of the cells C, C . . . and the blank cells K, K, . . . may be changed to other numbers and arrangement. The condition to determine the chest portion may be changed so as to satisfy independent individual conditions of the cells C, C . . . on the left side and the cells C, C . . . on the right side such that the sum of the pressure values 42, 42 . . . of the cells C, C . . . on the left side and the sum of the pressure values 42, 42 . . . of the cells C, C . . . on the right side become not smaller than the predetermined threshold values, respectively.

Figure 13B:
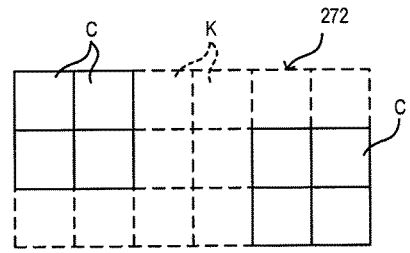
FIG. 13B is a schematic drawing of a modification thereof.

In addition, even when the sleeper A turns over to some extent, a supine chest specified pattern 272 illustrated in FIG. 13B or a supine chest specified pattern in lateral symmetry therewith can be scanned together with the supine chest specified pattern 271 for the purpose of detecting the chest position in the supine position with high degree of accuracy. In this case, in the case of no-detection in the scan with the supine chest specified pattern 271, the supine chest specified pattern 272 is scanned and if it is still not detected, the scanning with the pattern symmetry therewith may be performed.

When the control unit 69 detects the chest in the supine position under the above condition, the range of the cells C, C . . . is stored in the storage unit 62 as the supine chest detection position information. Further, ranges of the cells C, C . . . and the blank cells K, K, . . . are stored in the storage unit 62 as the chest respiration measurement position information 111.

The information to be stored may be changed as needed such that the supine chest detection position information is limited to a range of the cells C, C . . . and the blank cells K, K . . . or the chest respiration measurement position information 111 is set to a range larger than the above-described range.

In the position-detecting device (respiration measurement device and the heart rate measurement device) of the second embodiment, in the case where the pressure values 42, 42 . . . which match the specific pattern exist in the body pressure distribution information 44, it is not necessary to refer to the body pressure distribution information 44 from the matched pressure values 42, 42 . . . onward. The pressure values 42, 42 . . . which match the specific pattern, that is, the target body part can be detected accurately without determining all of the pressure values 42, 42 . . . of the body pressure distribution information 44. Therefore, position detection providing a high processing speed and an accurate processing result can be performed.

The position-detecting device, the respiration measurement device, and the heart rate measurement device of the present invention have an application as a component of a sleep apnea state detecting apparatus configured to detect the chest and the lower back accurately, figure out phase displacement between the chest respiration and the abdominal respiration or increase in the number of heart rates further accurately by continuous acquisition of the respective measurement values, and detect the sleep apnea state accurately.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

What is claimed is:

1. A position-detecting device comprising:
a body pressure distribution sensor including a plurality of pressure sensors that are capable of outputting pressure signals corresponding to pressure values respectively and are arranged in a matrix pattern having rows and columns, the body pressure distribution sensor being placed on bedclothes;
a storage that stores a specific pattern in association with a sleeping posture and a body part, the specific pattern including a range occupied by at least two pressure sensors of the plurality of pressure sensors corresponding to the body part when a user takes the sleeping posture on the bedclothes, and a condition of the pressure values of the at least two pressure sensors within the range, the storage further storing instructions; and
a processor, when executing instructions stored in the storage, that performs a process comprising:
sequentially applying the specific pattern to body pressure distribution information, which is a set of the pressure values arranged in the matrix pattern, by sequentially moving a position of the specific pattern starting from a scan starting position to an adjacent position in a row direction or a column direction of the body pressure distribution information;
sequentially determining whether the condition is satisfied at each position of the specific pattern in the body pressure distribution information, while the specific pattern is sequentially applied to the body pressure distribution information; and
determining a position of the body part or a related body part in the corresponding sleeping posture on the basis of the position of the specific pattern in the body pressure distribution information where it is determined that the condition is satisfied.

2. The position-detecting device according to claim 1, wherein
the body part includes individual parts in pair of left part and right part or upper part and lower part of the user,
the related body part includes body parts relating to the pair of body parts;
the scan starting position of the individual parts is the left part or the right part, or the upper part or the lower part in the body pressure distribution information depending on a position of the body parts in pair, and
the range of sequential application of the specific pattern in the body pressure distribution information is limited to the left part or the right part, or the upper part or the lower part in the body pressure distribution information depending on the position of the individual body parts in pair.

3. The position-detecting device according to claim 1, wherein the condition is that, for a number of the pressure sensors smaller than the number of the at least two pressure sensors within the range, the pressure value output from each of the number of pressure sensors is not smaller than a predetermined threshold value.

4. The position-detecting device according to claim 1, wherein after it is determined that the condition is satisfied during the sequential determination, the processor stops further applying the specific pattern to the body pressure distribution information.

5. A respiration measurement device including the position-detecting device of claim 1, wherein the position of at least one of the body part and the related body part detected by the position-detecting device is a position of a chest of the user, and
the processor, when executing the instructions stored in the storage, further performs measurement of a chest respiration measurement value relating to chest respiration of the chest of the user on the basis of the position of the chest of the user detected by the position-detecting device.

6. The respiration measurement device according to claim 5, wherein
a measurement value group, in which a plurality of chest respiration measurement values are accumulated, is stored, and
a chest respiration measurement value, which has no autocorrelation with the measurement value group is excluded from the measurement value group.

7. The respiration measurement device according to claim 5, wherein the pressure values output from the body pressure distribution sensor of the position-detecting device are weighted depending on the arrangement of the pressure values at the detected position of the chest, to measure the chest respiration measurement value.

8. A respiration measurement device including the position-detecting device of claim 1, wherein the position of at least one of the body part and the related body part detected by the position-detecting device is a position of a lower back of the user, and
the processor, when executing the instructions stored in the storage, further performs measurement of an abdominal respiration measurement value relating to abdominal respiration of the lower back of the user on the basis of the position of the lower back of the user detected by the position-detecting device.

9. The respiration measurement device according to claim 8, wherein
a measurement value group, in which a plurality of abdominal respiration measurement values are accumulated, is stored, and
an abdominal respiration measurement value, which has no autocorrelation with the measurement value group is excluded from the measurement value group.

10. The respiration measurement device according to claim 8, wherein the pressure values output from the body pressure distribution sensor of the position-detecting device are weighted depending on the arrangement of the pressure values at the detected position of the lower back, to measure the abdominal respiration measurement value.

11. A heart rate measurement device including the position-detecting device of claim 1, wherein the position of at least one of the body part and the related body part detected by the position-detecting device is a position of a chest of the user, and
the processor, when executing the instructions stored in the storage, further performs measurement of a heart rate measurement value relating to a heart rate of the chest of the user on the basis of the position of the chest of the user detected by the position-detecting device.

12. The heart rate measurement device according to claim 11, wherein a heart rate measurement value group in which a plurality of heart rate measurement values are accumulated, is stored, and a heart rate measurement value, which has no autocorrelation with the heart rate measurement value group is excluded from the heart rate measurement value group.

13. The heart rate measurement device according to claim 11, wherein the pressure values output from the body pressure distribution sensor of the position-detecting device are weighted depending on the arrangement of the pressure values at the detected position of the chest, to measure the heart rate measurement value.

* * * * *